(12) United States Patent
Nicholls et al.

(10) Patent No.: US 8,491,618 B2
(45) Date of Patent: Jul. 23, 2013

(54) SKIN PRICKING APPARATUS

(75) Inventors: Clive Nicholls, Aylesbury (GB); Jeremy Marshall, Oxford (GB)

(73) Assignee: Owen Mumford Limited, Woodstock, Oxfordshire (GB)

( * ) Notice: Subject to any disclaimer, the term of this patent is extended or adjusted under 35 U.S.C. 154(b) by 393 days.

(21) Appl. No.: 11/792,483

(22) PCT Filed: Dec. 19, 2005

(86) PCT No.: PCT/EP2005/056924
§ 371 (c)(1),
(2), (4) Date: Jun. 7, 2007

(87) PCT Pub. No.: WO2006/067120
PCT Pub. Date: Jun. 29, 2006

(65) Prior Publication Data
US 2008/0004651 A1    Jan. 3, 2008

(30) Foreign Application Priority Data
Dec. 21, 2004  (GB) .................................. 0427892.5

(51) Int. Cl.
*A61B 17/32* (2006.01)
(52) U.S. Cl.
USPC ....................................................... 606/181
(58) Field of Classification Search
USPC ............ 606/181, 182, 183; 600/583; 30/366, 30/367
See application file for complete search history.

(56) References Cited

U.S. PATENT DOCUMENTS

| 4,616,649 | A | * | 10/1986 | Burns ............................ 606/182 |
| 4,677,979 | A | * | 7/1987 | Burns ............................ 606/172 |
| 4,869,249 | A | * | 9/1989 | Crossman et al. ............ 606/182 |
| 4,892,097 | A | * | 1/1990 | Ranalletta et al. ............ 606/182 |
| 5,212,879 | A |   | 5/1993 | Biro et al. |
| 5,356,420 | A |   | 10/1994 | Czernecki et al. |
| 5,366,469 | A |   | 11/1994 | Steg et al. |
| 5,421,347 | A | * | 6/1995 | Enstrom ........................ 600/567 |
| 5,529,581 | A |   | 6/1996 | Cusack |
| 5,545,173 | A |   | 8/1996 | Herbst |
| 5,584,846 | A |   | 12/1996 | Mawhirt et al. |
| 5,630,828 | A | * | 5/1997 | Mawhirt et al. ............... 606/187 |
| 5,749,886 | A | * | 5/1998 | Abidin et al. ................. 606/182 |
| 5,755,733 | A |   | 5/1998 | Morita |
| 5,851,215 | A |   | 12/1998 | Mawhirt et al. |
| 6,136,013 | A |   | 10/2000 | Marshall et al. |

(Continued)

FOREIGN PATENT DOCUMENTS

| DE | 100 10 694 | 9/2001 |
| EP | 0 582 226 | 2/1994 |
| WO | 2004/045409 | 6/2004 |

OTHER PUBLICATIONS

European Patent Office Communication, dated Jun. 22, 2009 and issued in corresponding European Patent Application No. 05823861.9-1265.

*Primary Examiner* — Thomas McEvoy
(74) *Attorney, Agent, or Firm* — Young & Thompson

(57) ABSTRACT

A skin pricking apparatus including a casing 1, a lancet 15 located within the casing, a firing button 9 arranged to transfer a user applied force to the lancet 15 to drive the lancet through the casing 1, and lancet retaining element 12, 13, 23*a,b* arranged to substantially prevent movement of the lancet 15 through the casing 1 until the user applied force exceeds a predefined threshold force.

24 Claims, 2 Drawing Sheets

U.S. PATENT DOCUMENTS

| | | | |
|---|---|---|---|
| 6,306,152 B1 * | 10/2001 | Verdonk et al. | 606/182 |
| 6,322,574 B1 * | 11/2001 | Lloyd et al. | 606/181 |
| 6,719,771 B1 | 4/2004 | Crossman | |
| 2002/0077650 A1 * | 6/2002 | Schraga | 606/182 |
| 2003/0153939 A1 | 8/2003 | Fritz et al. | |
| 2004/0133227 A1 * | 7/2004 | Shang et al. | 606/182 |

* cited by examiner

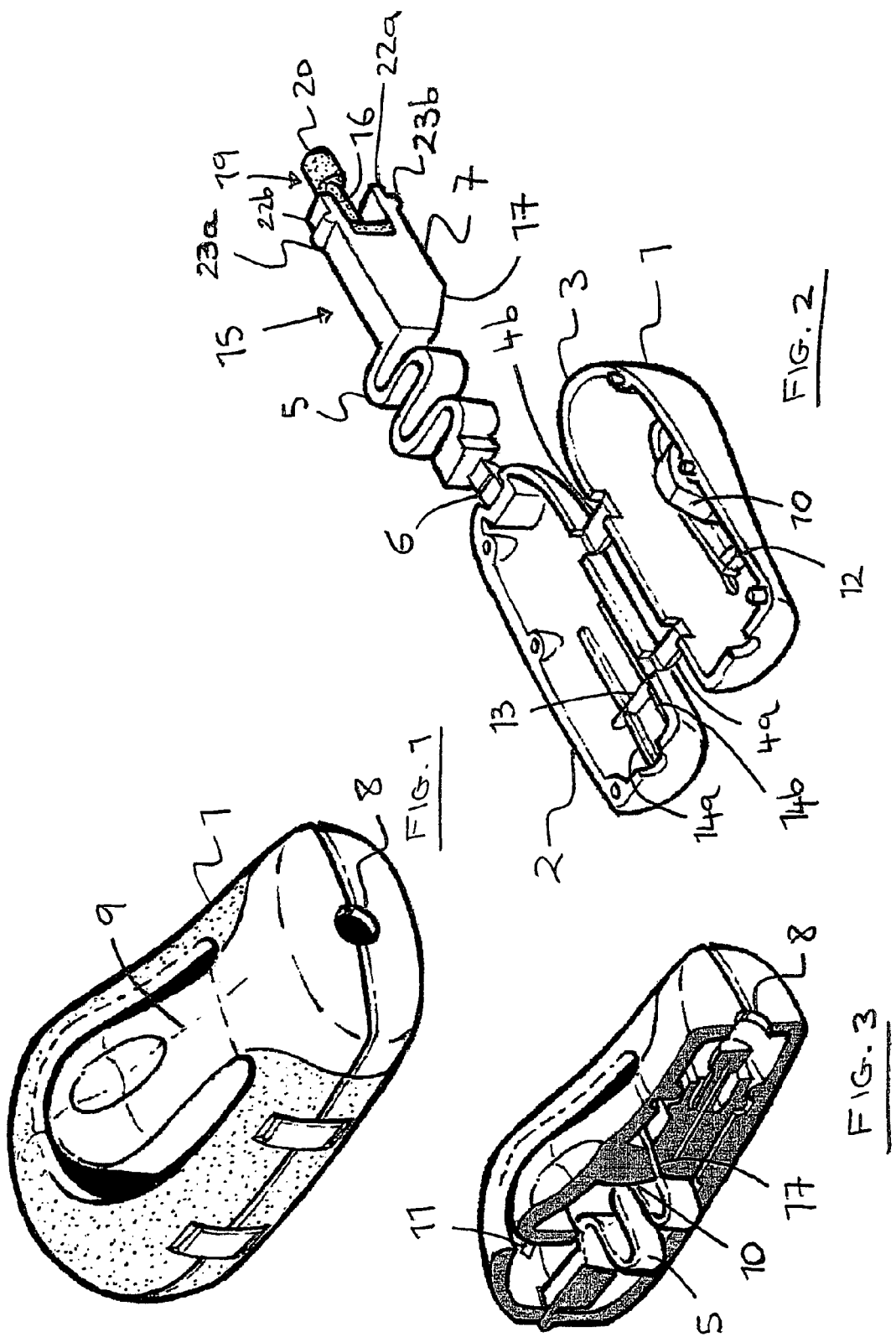

SKIN PRICKING APPARATUS

FIELD OF THE INVENTION

The present invention relates to skin pricking apparatus and in particular, though not necessarily, to a skin pricking apparatus for use in providing a sample of blood.

BACKGROUND

In the medical and related diagnostic and testing fields, it is often required to take small samples of blood from a subject for the purpose of testing or analysing the blood. A common way of achieving this is by using a small needle to pierce the skin at a location where blood vessels are close to the surface. The combination of a needle and its holder is commonly known as a lancet. In order to avoid infection and contamination, lancets are preferably intended for single use and are disposable. They must therefore be compact to allow users to carry multiple lancets on their person, and cheap to manufacture.

A number of disposable lancet devices are currently on the market. These include the Unistik™ manufactured and marketed by Owen Mumford Ltd (Woodstock, UK). The current designs comprise a moulded plastics casing within which is mounted a short, spring-loaded needle. A trigger is formed in the casing which, when depressed, releases the lancet causing the tip to be fired out through an opening in the casing. Some of the current designs require a user to preload or cock the spring prior to firing. In other designs, the lancet devices are supplied already cocked. It is also generally necessary for users to remove a cap from the front of the device or the needle tip prior to firing. Users must therefore perform at least two steps, and sometimes three, in order to perform the blood sampling procedure.

There exists a desire for a lancet device or apparatus which is simpler to operate than current designs. Of course, any improved design must meet high standards with regard to manufacturing costs. It must also be reliable, ensuring that lancet devices are provided to users in an operable condition.

SUMMARY OF THE INVENTION

According to a first aspect of the present invention there is provided a skin pricking apparatus comprising a casing, a lancet located within the casing, a firing button arranged to transfer a user applied force to the lancet to drive the lancet through the casing, and lancet retaining means arranged to substantially prevent movement of the lancet through the casing until the user applied force exceeds a predefined threshold force.

Embodiments of the present invention provide a lancet device which can be fired in an essentially one-step process. Nonetheless, accidental firing is unlikely, and the delivery of operable devices to users is ensured. Moreover, lancet devices embodying the invention are of relatively simple construction and have may have a lower component count than conventional designs.

In a preferred embodiment of the invention, said lancet retaining means comprises cooperating components on the casing and lancet. More preferably, these components comprise a first surface in which is formed a protrusion or recess and a second surface on which is formed a protrusion. The first and second surfaces may be provided on the inside of the casing and on the lancet respectively, or vice versa. The surfaces may be provided with a plurality of interengaging structural features.

In a preferred embodiment of the invention, said firing button is provided with an abutment surface arranged in use to contact a surface of the lancet in order to transfer said user applied force. More preferably, said surfaces are oriented obliquely with respect to the direction of travel of the lancet through the casing. This angle between the surfaces and this direction may be in the range 25-65 degrees, more preferably, 40-50 degrees, and more preferably still 45 degrees.

In a preferred embodiment of the invention, said firing button is moveable upon the application of a user force in a direction substantially perpendicular to the direction of travel of the lancet through the casing. Preferably, the firing button is formed integrally with the casing.

In a preferred embodiment of the invention, the apparatus comprises biasing means coupled between the lancet and the casing for biasing the lancet to a withdrawn position within the casing, the spring being extended by the application of said driving force to the lancet. Said biasing means may be a platform spring, moulded integrally with the casing and firing button.

Preferably, the lancet comprises a plastics body and a lancet needle embedded at one end within the body. More preferably, the lancet body is molded integrally with the casing. More preferably, the lancet body is molded integrally with the platform spring.

In a preferred embodiment, the lancet needle is shielded by a protective cover. More preferably, this cover is a moulded flexible plastics sheath, e.g. of thermoplastic elastomer.

In a preferred embodiment, the firing button comprises means for latching the button into a depressed position following depression and firing of the button, in order to prevent reuse of the apparatus and to provide a visual indication that the device has been used. More preferably, the latching means is a latch arranged to engage a lip formed in an opening in the casing.

According to a second aspect of the present invention there is provided a skin pricking apparatus comprising a casing, a lancet located within the casing and comprising a lancet driver plate, and a firing button resiliently coupled to the casing and comprising a lancet driver member, whereby depression of the firing button brings the lancet driver member into contact with the lancet driver plate and transfers a user applied force from the firing button to the lancet, the apparatus further comprising cooperating features on the casing and the lancet which substantially prevent movement of the lancet through the casing until the user applied force exceeds a predefined threshold force.

DESCRIPTION OF THE DRAWINGS

For a better understanding of the present invention and in order to show how the same may be carried into effect reference will now be made by way of example to the accompanying drawings in which:

FIG. 1 is a perspective view of a single use lancet device;

FIG. 2 is a perspective view of a moulded component used to form a casing of the lancet device of FIG. 1;

FIG. 3 is a perspective cross-sectional view of the lancet device of FIG. 1;

DETAILED DESCRIPTION OF THE INVENTION

Figure 4:
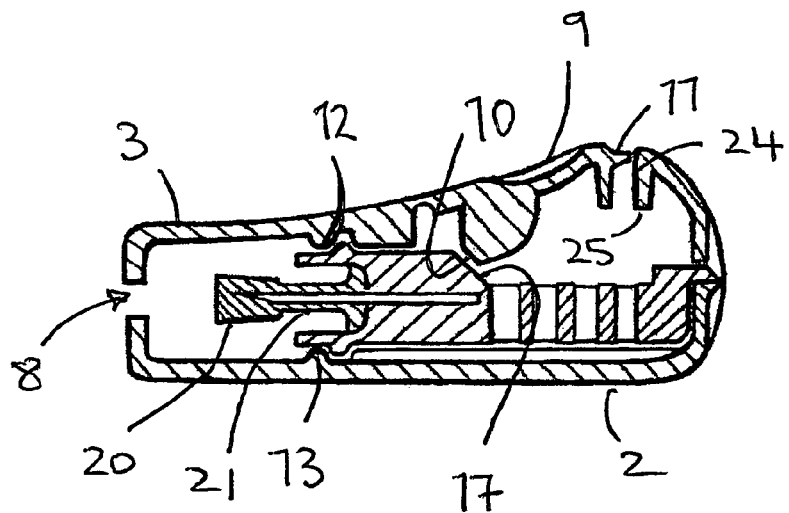
FIGS. 4 to 6 show vertical cross-sectional views of the device of FIG. 1 in various operational configurations.

There is illustrated in FIG. 1 an assembled single use lancet device designed for pricking a users skin to provide a small blood sample. Typically a user pricks the pad of his or her finger, leaving a small spot of blood on the finger. This spot can then be collected, e.g. using a test strip, for use in performing some measurement or test. The lancet device of FIG. 1 is formed from a single molded plastics component 1 illustrated in FIG. 2.

With reference to FIG. 2, the molded component 1 comprises a lower casing section 2 and an upper casing section 3 which are secured together by a pair of flexible hinges 4a,4b. A molded platform spring 5 is formed integrally with the casing components, and is attached to the lower casing component 2 by a flexible hinge 6. A lancet body 7 is also formed integrally with the casing components, and is fixed to the end of the platform spring 5 remote from the casing. As will be readily apparent from FIG. 3, which shows a vertical cross-section through the device of FIG. 1, the device is assembled by folding the spring and lancet into the lower casing section 2, about the hinge 6. The upper and lower casing sections are then folded together about the hinges 4a,4b. The upper and lower casing sections are provided with semi-circular recesses in one end wall which, when the device is folded together, combine to provide a circular opening 8.

Considering first the upper casing section 3, this comprises a trigger button 9 which is free on three sides but which is integral with the body of the casing on a fourth side, i.e. the side closest to the rear of the device. The trigger button 9 is able to flex at the point of attachment to the casing body so that it can be pressed downward (as viewed in FIG. 1) by finger pressure. Depending from the lower surface of the trigger button (again as viewed in FIG. 1) are a lancet driver 10 and a latch 11. In front of the trigger button 9, towards the opening 8, a blocking rib 12 depends from the inner surface of the upper casing section. A corresponding blocking rib 13 depends from the inner surface of the lower casing section. A pair of lancet guide rails 14a,14b are formed on the inner surface of the lower casing section.

A lancet 15 is provided by the lancet body 7 and a lancet needle 16 which is embedded at one end in the body 7. An angled drive plate 17 of the lancet body 7 provides a surface for engaging the lancet driver 10 as will be described below. A sharpened tip 18 projects outwardly from the lancet body 7 and, when the device is assembled, is aligned with the opening 8 formed in the end of the casing. The exposed portion of the needle 16 including the tip 18 is overmolded with a flexible and elastic plastics cover 19, e.g. of thermoplastic elastomer (TPE) such as SANTOPRENE or EVOPRENE (alternatively, the material may be polyurethane or polyurethane foam, silicon rubber, or liquid silicon rubber). The cover 19 has an enlarged, generally frustoconical shaped, head 20, which covers the tip of the needle (this feature is preferred, but not essential). The overmolding narrows in a stepwise manner to provide a narrow sleeve 21 which covers the remainder of the needle 16. The overmolding also covers the end surface of the body 7. The overmolding ensures sterility of the needle prior to use. Flexible fingers 22a,22b extend outwardly from the upper and lower surfaces of the lancet body, partially overlapping the lancet needle 16. Ribs 23a,23b are formed on the outwardly facing surfaces of respective fingers.

The casing comprises a number of components which mate together once the casing is folded, and which allow the various components of the lancet to be secured in place. These are apparent from the Figures, but will not be explained in any further detail as their construction and function will be readily apparent to the person of skill in the art.

When the device is folded together, the ribs 23a,23b on the lancet body 7 locate directly behind the blocking ribs 12 and 13 formed on the upper and lower casing sections, and the lancet body locates between the guide rails 14a,14b. In this state, the platform spring 5 is not subject to any compression or expansion force. In the assembled configuration, the lancet driver 10 sits above and out of contact with the angled drive plate 17 of the lancet body 7. This configuration is illustrated in the vertical cross-sectional view of FIG. 4.

Figure 5:
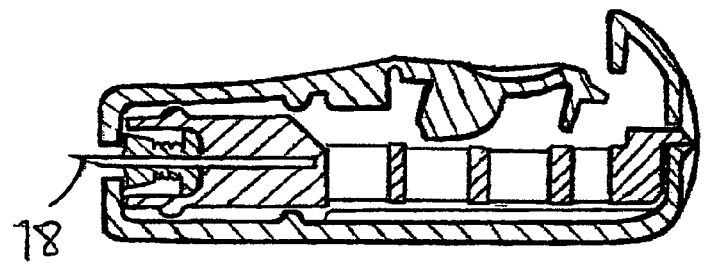
Figure 6:
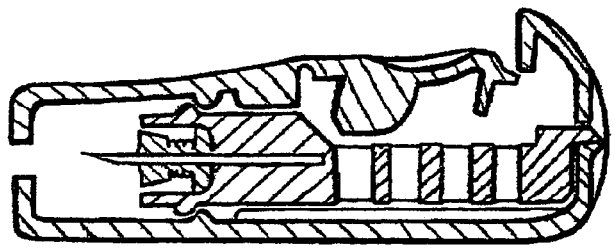

Operation of the lancet device will now be described with reference to FIGS. 4 to 6. In the pre-use configuration illustrated in FIG. 4, the trigger button 9 is in its resting position, with the lancet driver 10 sitting above, but not in contact with, the drive plate 17 of the lancet body 7. In order to operate the lancet, a user holds the lancet device in one hand, with his or her thumb placed over the firing button 9. The end of the device at which the opening 8 is located is then brought into contact with the area of skin to be pricked, e.g. the pad of a finger on the user's other hand. The user then depresses the trigger button 9, bringing the lancet driver 10 into contact with the drive plate 17 of the lancet body 7, tending to drive the lancet 15 towards the opening 8 in the casing. However, after a possibly short travel of the lancet 15 towards the opening, the ribs 23a,23b on the lancet body 7 engage the respective ribs 12,13 on the upper and lower casing sections, blocking further motion. The user will sense this resistance, and will increase the pressure applied to the trigger button 9.

When some predefined pressure is reached, e.g. say 5 to 10N, the fingers 22a,22b on which the ribs are formed will have flexed inwardly sufficient to release the lancet 15 for further travel. At this point, the user applied force remains high, and the lancet 15 will snap quickly past the ribs whilst experiencing a relatively "explosive" propelling force. This force is significantly greater than the resistance provided by the now expanding platform spring 5.

The lancet 15 travels through the casing until the head 20 of the overmolded section on the needle 16 contacts the inner surface of the opening 8 in the casing, surrounding the opening. This prevents further progress of the head. However, a force is still being exerted on the back of the lancet by the lancet driver 10, causing the needle tip 18 to be driven through the head 20. The sleeve 21 tends to concertina around the needle 16. The needle tip 18 is driven out through the opening 8 in the casing, and pierces the skin of the user. This is the configuration illustrated in FIG. 5. (In an alternative arrangement, the opening 14 may be large enough to allow passage of the head 29, in which case the user's skin provides the stop surface for the head.)

The dimensions of the lancet device are such that, at some point in the travel of the lancet 15 prior to the needle tip 18 exiting the opening 8, the drive plate 17 of the lancet body 7 has moved sufficiently to separate from the lancet driver 10. However, the momentum of the lancet 15 is sufficient to propel the needle tip out of the opening into contact with the user's skin. Once this kinetic energy has been spent, the platform spring 5 will begin to contract, pulling the lancet 15 and with it the needle tip 18 back inside the casing. It is noted that the overmolded cover 19 on the lancet needle tends to remain in a partially compressed state, and does not expand to recover the needle tip 18. This used configuration is illustrated in FIG. 6.

The purpose of the latch 11 formed on the inner surface of the trigger button 9 is to prevent reuse of the lancet device. As is seen in FIG. 6, the latch 11 slides across the opposed surface 24 of the upper casing section 3, before snapping behind the lower lip 25 of that surface. The resistance presented between the latch and the wall surface is easily overcome by the force which the user applies to release the lancet 15 from within the casing.

It will be appreciated by the person of skill in the art that various modifications may be made to the above described embodiments without departing from the scope of the present invention. In one such modification, the lancet body may be molded as a separate component with the needle embedded in the body to form the lancet, the lancet being placed inside the casing during assembly. The platform spring 5 may also be a separate component, or could be molded integrally with the lancet body or the casing.

The invention claimed is:

1. A skin pricking apparatus comprising:
   a casing;
   a lancet located within the casing;
   a firing button arranged to accept a user applied force,
      said firing button being provided with an abutment surface arranged in use to contact a surface of the lancet upon movement of the button in order to transfer said applied force to the lancet, the user applied force being transferred via said abutment surface and said surface of the lancet so that the user applied force drives the lancet linearly through the casing, said abutment surface and said lancet surface being oriented obliquely with respect to the direction of travel of the lancet through the casing;
   lancet retaining components arranged to prevent said linear movement of the lancet through the casing until the user applied force exceeds a predefined threshold force,
   said lancet retaining components comprising cooperating structural features on an inside of the casing and on an outer surface of the lancet respectively, said features arranged to be in abutment prior to said user applied force exceeding said predefined threshold force; and
   a spring coupled between the lancet and the casing for biasing the lancet to a withdrawn position within the casing, the spring being extended by the application of the user applied force to the lancet.

2. The apparatus according to claim 1, said firing button being moveable upon the application of the user applied force in a direction substantially perpendicular to the direction of travel of the lancet through the casing.

3. The apparatus according to claim 1, said firing button being formed integrally with the casing.

4. The apparatus according to claim 1, said spring being molded integrally with the casing.

5. The apparatus according to claim 1, the lancet comprising a plastic body and a lancet needle embedded at one end within the body, the lancet body being molded integrally with the casing.

6. The apparatus according to claim 1, the lancet comprising a needle tip, the needle tip of the lancet being shielded by a protective cover which is an overmolded flexible plastic sheath.

7. The apparatus according to claim 1, the firing button comprising means for latching the button into a depressed position following depression and firing of the button, in order to prevent reuse of the apparatus.

8. The apparatus according to claim 7, the latching means comprising a latch arranged to engage a lip formed in an opening in the casing.

9. The apparatus according to claim 1, further comprising a pair of lancet guide rails formed on an inner surface of the casing, wherein the lancet is positioned between each rail of the pair of guide rails, and the guide rails guide the lancet linearly through the casing.

10. The apparatus according to claim 1, wherein the spring is extended by the application of the user applied force to the lancet while the lancet is driven linearly through the casing toward the user's skin.

11. The apparatus according to claim 1, wherein the spring is extended in a longitudinal direction by the application of the user applied force to the lancet.

12. The apparatus according to claim 1, wherein the firing button is flexibly coupled to the casing, and the spring is attached to, or integral with, the casing.

13. The apparatus according to claim 1, wherein the firing button is arranged to transfer the accepted user applied force to the lancet such that the user applied force imparts a momentum on the lancet to drive the lancet linearly through the casing, and the lancet capable of being driven into the skin by the momentum of the lancet.

14. A skin pricking apparatus comprising:
   a casing;
   a lancet located within the casing and comprising a lancet driver plate;
   a firing button resiliently coupled to the casing and comprising a lancet driver member, whereby depression of the firing button brings surfaces of the lancet driver member and lancet driver plate into abutting contact and transfers a user applied force from the firing button to the lancet to drive the lancet linearly through the casing, the abutting surfaces being oriented obliquely with respect to the direction of travel of the lancet through the casing, the firing button being moveable, upon the application of the user applied force, in a direction substantially perpendicular to the direction of travel of the lancet through the casing;
   cooperating structural features on the casing and on the lancet which substantially prevent movement of the lancet through the casing until the user applied force exceeds a predefined threshold force; and
   a planar spring coupled between the lancet and the casing for biasing the lancet to a withdrawn position within the casing, the spring being extended by the application of the driving force to the lancet.

15. The apparatus according to claim 14, said firing button being formed integrally with the casing.

16. The apparatus according to claim 14, said spring being molded integrally with the casing.

17. The apparatus according to claim 14, the lancet comprising a plastic body and a lancet needle embedded at one end within the body, the lancet body being molded integrally with the casing.

18. The apparatus according to claim 14, the lancet comprising a needle tip, the needle tip of the lancet being shielded by a protective cover which is an overmolded flexible plastic sheath.

19. The apparatus according to claim 14, the firing button comprising means for latching the button into a depressed position following depression and firing of the button, in order to prevent reuse of the apparatus.

20. The apparatus according to claim 19, the latching means comprising a latch arranged to engage a lip formed in an opening in the casing.

21. The apparatus according to claim 14, further comprising a pair of lancet guide rails formed on an inner surface of the casing, wherein the lancet is positioned between each rail of the pair of guide rails, and the guide rails guide the lancet linearly through the casing.

22. The apparatus according to claim 14, wherein the spring is extended in a longitudinal direction by the application of the user applied force to the lancet.

23. The apparatus according to claim 14, wherein the firing button is flexibly coupled to the casing, and the spring is attached to, or integral with, the casing.

24. The apparatus according to claim 14, wherein the firing button is arranged to transfer the user applied force to the lancet such that the user applied force imparts a momentum on the lancet to drive the lancet linearly through the casing, and the lancet is capable of being driven into the skin by the momentum of the lancet.

* * * * *

UNITED STATES PATENT AND TRADEMARK OFFICE
CERTIFICATE OF CORRECTION

PATENT NO. : 8,491,618 B2  Page 1 of 1
APPLICATION NO. : 11/792483
DATED : July 23, 2013
INVENTOR(S) : Nicholls et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 223 days.

Signed and Sealed this
Eighth Day of September, 2015

Michelle K. Lee
*Director of the United States Patent and Trademark Office*